United States Patent [19]

Cesa

[11] Patent Number: 5,099,066
[45] Date of Patent: Mar. 24, 1992

[54] SYNTHESIS OF N-SUBSTITUTED AMIDES BY CONDENSATION OF NITRILES WITH CERTAIN ORGANIC HYDROXYL COMPOUNDS

[75] Inventor: Mark C. Cesa, South Euclid, Ohio

[73] Assignee: The Standard Oil Company, Cleveland, Ohio

[21] Appl. No.: 515,902

[22] Filed: Apr. 27, 1990

[51] Int. Cl.$^5$ ............................................. C07C 231/06
[52] U.S. Cl. ..................... 564/130; 564/131; 260/404
[58] Field of Search ..................... 564/130, 126, 131; 260/404

[56] References Cited

FOREIGN PATENT DOCUMENTS

| | | | |
|---|---|---|---|
| 1009614 | 6/1957 | Fed. Rep. of Germany | 564/130 |
| 1229618 | 4/1971 | United Kingdom | 564/130 |

OTHER PUBLICATIONS

The Condensed Chemical Dictionary, 8th edition, p. 96, 1974.
Chemical Abstract, vol. 74: 124883n, 1971.

*Primary Examiner*—Richard L. Raymond
*Assistant Examiner*—John D. Pak
*Attorney, Agent, or Firm*—C. S. Lynch; M. F. Esposito; L. W. Evans

[57] ABSTRACT

Disclosed is a method which comprises the reaction in a reaction zone of a nitrile, RCN, with a hydroxyl compound, R'OH, in the presence of a Lewis base as catalyst introduced into the reaction zone, thereby producing a reaction mixture containing at least one amide selected from R—CONHR' and R—CON(R')$_2$, wherein each of R and R' contains no acetylenic unsaturation and 1 to 30 carbon atoms, each of R and R' is independently selected from a hydrocarbyl group and a hydrocarbyl group that is substituted with a group selected from cyano, carbamoyl, hydrocarbylcarbamoyl, dihydrocarbylcarbamoyl, and hydroxyl.

7 Claims, No Drawings

SYNTHESIS OF N-SUBSTITUTED AMIDES BY CONDENSATION OF NITRILES WITH CERTAIN ORGANIC HYDROXYL COMPOUNDS

This invention relates to the synthesis of N-substituted amides by condensation of nitriles with certain organic hydroxyl compounds. In particular, the invention relates to such a process using organic and inorganic bases as catalysts for such reaction.

The important solvent, N,N-dimethylacetamide, is currently prepared industrially from acetic acid and dimethylamine. It is a superior organic solvent, with high boiling range and good thermal stability relative to other amides such as dimethylformamide. The current DMAC synthesis suffers from relatively high raw material costs. As a result, DMAC has a high price (about $1.00 per pound). This high price precludes use of DMAC in many applications where relatively inferior but lower priced solvents are used.

The process of the present invention has the potential to lower N-substituted amides production costs substantially because of the much lower prices of the starting materials compared with the price of the raw materials of the current synthetic method, thus offering the potential for growth of DMAC demand into applications where its superior properties would be an advantage.

It is an object of the present invention to provide an improved process of making N-substituted amides.

It is a further object of the invention to lower the cost of making N-substituted amides by condensing nitriles with alcohols in the presence of base catalysts.

Other objects, as well as aspects and advantages, of the invention will become apparent from a study of the specification, including the specific examples and the claims.

The foregoing and other objects are realized by the present invention according to which there is provided a method which comprises the reaction in a reaction zone of a nitrile, RCN, with a hydroxyl compound, R'OH, in the presence of a Lewis base as catalyst introduced into the reaction zone, thereby producing a reaction mixture containing at least one amide selected from R—CONHR' and R—CON(R')$_2$, wherein each of R and R' contains no acetylenic unsaturation and 1 to 30 (usually 1 to 12) carbon atoms, each of R and R' is independently selected from a hydrocarbyl group and a hydrocarbyl group that is substituted with a group selected from cyano, carbamoyl, hydrocarbylcarbamoyl, dihydrocarbylcarbamoyl, and hydroxyl.

Some Lewis base catalysts are ammonia; mono-, di-, and trihydrocarbylamines; heterocyclic nitrogen compounds such as, for example, pyridines; and hydroxides of elements of Group 1 and Group 2 having atomic weights less than 145; and catalysts of the above description supported on or incorporated into solid organic polymer supports or solid inorganic supports such as silica, alumina, magnesia, kieselguhr, and pumice.

The Groups refer to the Periodic Table of the Elements that numbers the groups from 1 to 18, appearing in *Chemical and Engineering News*, Feb. 4, 1985, p. 27.

The hydrocarbylamine catalysts usually used have the formula R$_1$R$_2$R$_3$N, where each of R$_1$, R$_2$, and R$_3$ is independently selected from H, a C$_1$-C$_{12}$ hydrocarbyl group containing no ethylenic or acetylenic unsaturation; and a substituted C$_1$-C$_{12}$ hydrocarbyl group containing no ethylenic or acetylenic unsaturation, where said substituent is a —NR$_4$R$_5$ group, where R$_4$ and R$_5$ are independently selected from H and a C$_1$-C$_4$ alkyl group.

The heterocyclic nitrogen compound catalysts usually used have the formula

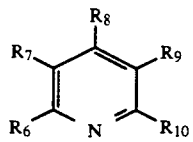

where R$_6$, R$_7$, R$_8$, R$_9$, and R$_{10}$ are each independently selected from H, a C$_1$-C$_{12}$ hydrocarbyl group containing no ethylenic or acetylenic unsaturation; 2-pyridyl; 3-pyridyl; and a substituted C$_1$-C$_{12}$ hydrocarbyl group containing no ethylenic or acetylenic unsaturation, where said substituent is a —NR$_4$R$_5$ group where R$_4$ and R$_5$ are independently selected from H and a C$_1$-C$_4$ alkyl group.

Optimum catalyst amounts can be determined by routine experiments, but often vary from 0.0001 to 10 moles introduced into the reaction zone per 100 moles of the nitrile, RCN, introduced into the reaction zone. More usually the amount is from 0.01 to 5 moles per 100 moles of the nitrile, RCN.

In the process of the present invention a number of side reactions occur, producing numerous by-products in addition to the N-Substituted amides R—CONHR' and R—CON(R')$_2$. Typically, such by-products include mono-, di- and trimethyl amines, methyl acetate, water, acetic acid, and acetamide, where the charge reactants are acetonitrile and methanol, for instance.

In one aspect of practising the invention we contemplate recycling the reactor effluent to the reaction zone after first removing the R—CON(R')$_2$ product, acetic acid and possibly, water. This recycle stream is augmented by fresh RCN and R'OH feed to the reaction zone. This recycle procedure increases the overall yield and selectivity to R—CON(R')$_2$ based on fresh RCN charged to the reaction zone.

In another aspect of the invention we contemplate charging to the reaction zone a crude cut from the effluent of an ammoxidation reaction for making acrylonitrile, for instance, from propylene or from propane. Thus, a partially purified acetonitrile cut separated from the ammoxidation reactor effluent can be all or part of the acrylonitrile charge to the reaction zone of this invention. This cut is mainly acetonitrile and water, but also contains small amounts of other components such as acrylonitrile, methacrylonitrile, propionitrile, pyridine, methyl-substituted pyridine(s), oxazole, pyrazine, benzonitrile, cyanopyridine, cyano-furans and aniline.

The condensation of nitriles with alcohols to form N-substituted amides is known as the Ritter reaction. Typical Ritter reaction catalysts are mineral acids, such as H$_2$SO$_4$ or H$_3$PO$_4$. The Ritter reaction is usually thought of as a reaction between a nitrile and a secondary or tertiary alcohol, which can readily form a carbonium ion in the presence of mineral acid. The carbonium ion then reacts with the nitrile in the key step in amide formation. See, for example, W. F. Gresham and W. E. Grigsby, U.S. Pat. No. 2,601,387.

Formation of amides from nitriles and primary alcohols, e.g. methanol, requires more severe conditions. A series of patents to Asahi (U.S. Pat. No. 3,751,465; JP 73 03,813; GB 1,229,618, Chemical Abstracts 74, 124883n and 76, 139955c) describe the use of catalysts such as transition metal salts for synthesis of DMAC from acetonitrile and methanol at high temperatures (up to 400° C. or higher) in stirred autoclaves. There are, however, no known literature or patent references to the use of a base as a catalyst for this amide synthesis reaction.

According to the present invention, the base catalyzed synthesis of amides from nitriles and alcohols can be carried out in either the vapor phase or in the liquid phase, at atmospheric pressure or reduced or elevated pressure, in a batch mode, flow mode or continuous stirred reactor mode. If byproduct recycle is desired, the recycle process can be carried out continuously or in a batch mode. In an especially effective embodiment of the invention, applied to the synthesis of, for example, N,N-dimethylacetamide (DMAC) from acetonitrile and methanol, a continuous stirred reactor system can be used in which reaction byproducts and unreacted starting materials (recovered by distillation) are recycled to the reaction zone with fresh starting materials, with flows balanced so that an essentially constant DMAC synthesis rate is established with essentially no net byproduct synthesis.

The presence of inert diluents for any of the starting materials is within the scope of the invention. For example, the use of nitrogen or other inert gas in the reaction zone is permitted, and is favored in high-temperature liquid phase conditions to minimize unwanted side reactions. Also, the use of inert solvents with the reactants such as, for example (but not restricted to), alkanes and aromatic hydrocarbons is within the scope of the invention.

The reactants can be employed from the beginning of the reaction in the full amounts required for the reaction, or the reactants can be introduced to the reaction zone successively or stepwise during the course of the reaction.

It has also been found that water can improve N,N-disubstituted amide yield or selectivity in the base catalyzed reactions. When water is used it is used in the amount of up to 10 moles, usually no more than 2 moles, introduced into the reaction zone, per mole of RCN introduced into the reaction zone.

The process of this invention can be carried out at from 100° C. to 600° C. Optimum temperatures depend on the particular reactants and other parameters easily determined by routine test. For instance, primary alcohols usually require higher temperatures than secondary and tertiary alcohols.

Pressures can range from 0.1 atmosphere to 200 atmospheres or more. In liquid phase runs carried out in pressure vessels with low-boiling reactants, high reaction temperatures required for sufficient reaction rates result in pressures well above 1 atmosphere, as in the case of the specific examples herein.

The alcohol/nitrile mole ratio can range from 0.1 to 3, but usual ratios range from 1.0 to 2.5. Lower amounts of alcohol relative to nitrile result in promotion of formation of N-monosubstituted amide, and higher amounts sometimes can alcoholyze amide products, lowering yield of desired product. It should be noted that formation of appreciable amounts of N-monosubstituted amide is not necessarily a disadvantage. First, if this is desired as a co-product, or in the second instance if a recycle process be used. In the latter event the N-substituted amide is a very efficacious feed to the reaction zone, where it helps maintain the equilibrium between this by-product and all other reaction products.

The process of the present invention does not involve the intentional addition of molecular oxygen into the reaction zone, because of loss of product by oxidation.

The following examples of the invention are exemplary and should not be taken as in any way limiting.

EXAMPLE 1

A mixture of acetonitrile (31.63 g, 0.7705 mol), methanol (32.04 g, 0.9999 mol), and pyridine (1.85 g, 0.0234 mol) was placed in a stainless steel autoclave of 300 mL internal volume. The reactor was sealed, and the reaction mixture was purged with nitrogen through a dip tube for 30 minutes. The reactor was then heated to 342° C., and the reaction mixture was stirred vigorously. The temperature of the reaction mixture reached 392° C., and the reaction mixture was stirred at that temperature for 4 hours. The reactor was then cooled, and the reaction mixture was analyzed by gas chromatography. Conversion of methanol was 95.1% and conversion of acetonitrile was 75.9%. Product yields (based on acetonitrile) were as follows: methylamine 1.9%, dimethylamine 9.7%, methyl acetate 0.8%, N,N-dimethylacetamide (DMAC) 14.8%, acetic acid 8.7%, N-methylacetamide 21.7%, and acetamide 31.1%.

COMPARATIVE EXAMPLE A

A mixture of acetonitrile (31.57 g, 0.7690 mol) and methanol (32.04 g, 0.9999 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 353° C., and the reaction mixture was stirred at that temperature for 4 hours. The reactor was then cooled, and the reaction mixture was analyzed by gas chromatography. Conversion of methanol was 37.8% and conversion of acetonitrile was 20.4%. Product yields (based on acetonitrile) were as follows: methylamine 2.6%, dimethylamine 5.6%, methyl acetate 12.2%, N,N-dimethylacetamide (DMAC) 0.5%, acetic acid 0.3%, N-methylacetamide 3.3%, and acetamide 4.1%.

EXAMPLE 2

To simulate recycle conditions, a mixture of acetonitrile (9.32 g, 0.2270 mol), methanol (15.02 g, 0.4688 mol), pyridine (1.84 g, 0.0233 mol), methylamine (0.68 g, 0.0219 mol), dimethylamine (4.76 g, 0.1056 mol), methyl acetate (0.48 g, 0.0065 mol), acetic acid (4.16 g, 0.0693 mol), N-methylacetamide (13.51 g, 0.1848 mol), and acetamide (14.20 g, 0.2404 mol) was placed in a stainless steel autoclave of 300 mL internal volume. The reactor was sealed, and the reaction mixture was purged with nitrogen through a dip tube for 30 minutes. The reactor was then heated to 350° C., and the temperature of the reaction mixture reached 367° C. The reaction mixture was stirred for 3 hours during this time. The reactor was then cooled, and the reaction mixture was analyzed by gas chromatography. Conversion of methanol was 92.0% and conversion of acetonitrile was 71.9%. N,N-dimethylacetamide yield (based on acetonitrile) was 77.0%.

COMPARATIVE EXAMPLE B

To simulate recycle conditions, a mixture of acetonitrile (12.12 g, 0.2952 mol), methanol (19.51 g, 0.6089 mol), methylamine (0.71 g, 0.0229 mol), dimethylamine (6.73 g, 0.1493 mol), methyl acetate (1.01 g, 0.0136 mol) acetic acid (3.58 g, 0.0596 mol), N-methylacetamide (25.92 g, 0.3546 mol), and acetamide (19.05 g, 0.3225 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 376° C., and the reaction mixture was stirred for 3 hours. The reactor was then cooled, and the reaction mixture was analyzed by gas chromatography. Conversion of methanol was 71.3% and conversion of acetonitrile was 71.3%. N,N-dimethylacetamide yield (based on acetonitrile) was 85.1%.

EXAMPLE 3

A mixture of acetonitrile (31.58 g, 0.7693 mol), methanol (32.04 g, 0.9999 mol), and triethylamine (2.37 g, 0.0234 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 371° C., and the reaction mixture was stirred at that temperature for 2.75 hours. The reactor was then cooled, and the reaction mixture was analyzed by gas chromatography. Conversion of methanol was 55.4% and conversion of acetonitrile was 36.4%. Product yields (based on acetonitrile) were as follows: methylamine 1.7%, dimethylamine 8.7%, methyl acetate 13.9%, N,N-dimethylacetamide (DMAC) 1.5%, acetic acid 1.5%, N-methylacetamide 9.5%, and acetamide 14.2%.

EXAMPLE 4

A mixture of acetonitrile (31.62 g, 0.7702 mol), methanol (32.04 g, 0.9999 mol) and 4-methylpyridine (2.79 g, 0.0300 mol) was placed in a stainless steel autoclave of 300 mL internal volume. The reactor was sealed, and the reaction mixture was purged with nitrogen through a dip tube for 30 minutes. The reactor was then heated to 330° C., and the reaction mixture was stirred vigorously. The temperature of the reaction mixture reached 380° C., and the reaction mixture was stirred at that temperature for 4.5 hours. The reactor was then cooled, and the reaction mixture was analyzed by gas chromatography. Conversion of methanol was 91.3% and conversion of acetonitrile was 68.3%. Product yields (based on acetonitrile) were as follows: dimethylamine 15.4%, methyl acetate 3.3%, N,N-dimethylacetamide (DMAC) 5.5%, acetic acid 11.9%, N-methylacetamide 19.9%, and acetamide 30.3%.

EXAMPLE 5

A mixture of acetonitrile (31.58 g, 0.7693 mol), methanol (32.04 g, 0.9999 mol), and 2,4-dimethylpyridine (2.46 g, 0.0230 mol) was placed in a stainless steel autoclave of 300 mL internal volume. The reactor was sealed, and the reaction mixture was purged with nitrogen through a dip tube for 30 minutes. The reactor was then heated to 330° C., and the reaction mixture was stirred vigorously. The temperature of the reaction mixture reached 372° C., and the reaction mixture was stirred at that temperature for 4.5 hours. The reactor was then cooled, and the reaction mixture was analyzed by gas chromatography. Conversion of methanol was 64.1% and conversion of acetonitrile was 39.1%. Product yields (based on acetonitrile) were as follows: methylamine 1.1%, dimethylamine 12.5%, methyl acetate 14.8%, N,N-dimethylacetamide (DMAC) 1.7%, acetic acid 1.3%, N-methylacetamide 9.8%, and acetamide 16.6%.

EXAMPLE 6

A mixture of acetonitrile (31.62 g, 0.7702 mol), methanol (32.05 g, 1.0002 mol) and 2,4,6-trimethylpyridine (2.79 g, 0.0230 mol) was placed in a stainless steel autoclave of 300 mL internal volume. The reactor was sealed, and the reaction mixture was purged with nitrogen through a dip tube for 30 minutes. The reactor was then heated to 320° C., and the reaction mixture was stirred vigorously. The temperature of the reaction mixture reached 395° C., and the reaction mixture was stirred at that temperature for 4.5 hours. The reactor was then cooled, and the reaction mixture was analyzed by gas chromatography. Conversion of methanol was 77.2% and conversion of acetonitrile was 53.7%. Product yields (based on acetonitrile) were as follows: methylamine 1.6%, dimethylamine 20.7%, methyl acetate 9.9%, N,N-dimethylacetamide (DMAC) 3.9%, acetic acid 7.2%, N-methylacetamide 14.4%, and acetamide 22.5.

EXAMPLE 7

A mixture of acetonitrile (31.61 g, 0.7700 mol), methanol (32.06 g, 1.0006 mol) and aqueous ammonia (1.34 g, 29 weight % ammonia, 0.0229 mol $NH_3$) was placed in a stainless steel autoclave of 300 mL internal volume. The reactor was sealed, and the reaction mixture was purged with nitrogen through a dip tube for 30 minutes. The reactor was then heated to 340° C. and the reaction mixture was stirred vigorously. The temperature of the reaction mixture reached 370° C., and the reaction mixture was stirred at that temperature for 4.5 hours. The reactor was then cooled, and the reaction mixture was analyzed by gas chromatography. Conversion of methanol was 65.3% and conversion of acetonitrile was 45.9%. Product yields (based on acetonitrile) were as follows: dimethylamine 17.8%, methyl acetate 14.9%, N,N-dimethylacetamide (DMAC) 2.0%, acetic acid 3.9%, N-methylacetamide 11.7%, and acetamide 18.1%.

EXAMPLE 8

A mixture of acetonitrile (31.68 g, 0.7717 mol), methanol (32.04 g, 0.9999 mol), and NaOH (0.96 g, 0.0240 mol) was placed in a stainless steel autoclave of 300 mL internal volume. The reactor was sealed, and the reaction mixture was purged with nitrogen through a dip tube for 30 minutes. The reactor was then heated to 320° C., and the reaction mixture was stirred vigorously. The temperature of the reaction mixture reached 386° C., and the reaction mixture was stirred at that temperature for 4.5 hours. The reactor was then cooled, and the reaction mixture was analyzed by gas chromatography. Conversion of methanol was 91.0% and conversion of acetonitrile was 78.9%. Product yields (based on acetonitrile) were as follows: dimethylamine 15.4%, methyl acetate 1.5%, N,N-dimethylacetamide (DMAC) 16.0%, acetic acid 25.7%, N-methylacetamide 16.9%, and acetamide 11.6%.

EXAMPLE 9

A 46.13 g sample of crude acetonitrile of approximate composition 49.3 weight % acetonitrile, 42.3 weight % water, 0.3 weight % HCN, and the remainder acrylonitrile, propionitrile, methanol, oxazole, methacrylonitrile, pyridine, pyrazine, butenenitrile, and methylpyridines was combined with methanol (20.03 g, 0.6251 mol), and the mixture was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2.5 hours. The temperature of the reaction mixture reached 354° C. during this time. The reactor was then cooled, and the reaction mixture was analyzed by gas chromatography. Conversion of methanol was 90.6% and conversion of acetonitrile was 92.0%. Product yields (based on acetonitrile) were as follows: methylamine 0.3%, dimethylamine 4.9%, methyl acetate 0.6%, N,N-dimethylacetamide (DMAC) 14.7%, acetic acid 23.3%, N-methylacetamide 40.3%, and acetamide 22.2%.

EXAMPLE 10

To simulate recycle conditions, a 15.42 g sample of crude acetonitrile of approximate composition 49.3 weight % acetonitrile, 42.3 weight % water, 0.3 weight % HCN, and the remainder acrylonitrile, propionitrile, methanol, oxazole, methacrylonitrile, pyridine, pyrazine, butenenitrile, and methylpyridines was combined with methanol (11.88 g, 0.3708 mol), methylamine (0.34 g, 0.0109 mol), dimethylamine (2.01 g, 0.0446 mol), methyl acetate (0.29 g, 0.0039 mol), acetic acid (3.94 g, 0.0656 mol), N-methylacetamide (16.47 g, 0.2253 mol), and acetamide (7.33 g, 0.1241 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously for 2 hours. The temperature of the reaction mixture reached 370° C. during this time. The reactor was then cooled, and the reaction mixture was analyzed by gas chromatography. Conversion of methanol was 91.3% and conversion of acetonitrile was 83.8%. N,N-dimethylacetamide yield (based on acetonitrile) was 67.9%.

EXAMPLE 11

A mixture of acetonitrile (25.25 g, 0.6151 mol), ethanol (36.86 g, 0.8001 mol), and pyridine (1.46 g, 0.0185 mol) was placed in a stainless steel autoclave of 300 mL internal volume. The reactor was sealed, and the reaction mixture was purged with nitrogen through a dip tube for 30 minutes. The reactor was then heated to 302° C., and the reaction mixture was stirred vigorously. The temperature of the reaction mixture reached 365° C., and the reaction mixture was stirred at that temperature for 4 hours. The reactor was then cooled, and the reaction mixture was analyzed by gas chromatography. Conversion of ethanol was 54.5% and conversion of acetonitrile was 46.3%. Product yields (based on acetonitrile) were as follows: ethyl acetate 15.2%, N,N-diethylacetamide 0.3%, N-ethylacetamide 3.5%, acetic acid 0.8%, and acetamide 10.0%.

COMPARATIVE EXAMPLE C

A mixture of acetonitrile (25.43 g, 0.6195 mol) and ethanol (36.86 g, 0.8001 mol) was placed in a stainless steel autoclave of 300 mL internal volume. The reactor was sealed, and the reaction mixture was purged with nitrogen through a dip tube for 30 minutes. The reactor was then heated to 350° C., and the reaction mixture was stirred vigorously. The temperature of the reaction mixture reached 364° C., and the reaction mixture was stirred at that temperature for 4 hours. The reactor was then cooled, and the reaction mixture was analyzed by gas chromatography. Conversion of ethanol was 36.2% and conversion of acetonitrile was 19.7%. Product yields (based on acetonitrile) were as follows: ethyl acetate 8.4%, N,N-diethylacetamide 0.1%, N-ethylacetamide 0.6%, acetic acid 1.1%, and acetamide 2.6%.

As will be evident to those skilled in the art various modifications of this invention can be made or followed in the light of the foregoing disclosure and discussion without departing from the spirit and scope of the disclosure or from the scope of the claims.

I claim:

1. The reaction in a reaction zone of a nitrile, RCN, with a hydroxyl compound, R'OH, in the presence of a catalyst introduced into the reaction zone, thereby producing a reaction mixture containing at least one amide selected from R—CONHR' and R—CON(R')$_2$, wherein each of R and R' contains no acetylenic unsaturation and 1 to 30 carbon atoms, each of R and R' is an independently selected hydrocarbyl group, and wherein a hydroxide of an element of Group 1 or Group 2 said catalyst is a Lewis base selected from ammonia; of the Periodic Table referred to in the specification a hydroxide of an element selected from the group consisting of Groups 1 and 2 having an atomic weights less than 145; a hydrocarbyl amine having the formula

$R_1R_2R_3N$, where each of $R_1$, $R_2$, and $R_3$ is independently selected from H, a $C_1$-$C_{12}$ hydrocarbyl group containing no ethylenic or acetylenic unsaturation; and a substituted $C_1$-$C_{12}$ hydrocarbyl group containing no ethylenic or acetylenic unsaturation, where said substituent is a —NR$_4$R$_5$ group, where R$_4$ and R$_5$ are independently selected from H and a $C_1$-$C_4$ alkyl group; and a heterocyclic nitrogen compound having the formula

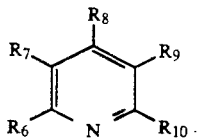

where R$_6$, R$_7$, R$_8$, R$_9$, and R$_{10}$ are each independently selected from H, a $C_1$-$C_{12}$ hydrocarbyl group containing no ethylenic or acetylenic unsaturation, 2-pyridyl, 3-pyridyl, and a substituted $C_1$-$C_{12}$ hydrocarbyl group containing no ethylenic or acetylenic unsaturation, where said substituent is a —$NR_4R_5$ group where $R_4$ and $R_5$ are independently selected from H and a $C_1$-$C_4$ alkyl group.

2. The reaction in a reaction zone of acetonitrile with methanol according to claim 1, thereby producing a reaction mixture containing dimethylacetamide.

3. A reaction according to claim 1 wherein each of R and R' contains no more than 12 carbon atoms.

4. The reaction of claim 1 wherein water as a reaction promoter is introduced into the reaction zone in the amount of up to 10 moles per mole of RCN introduced into said reaction zone.

5. The reaction of claim 1 wherein water as a reaction promoter is introduced into the reaction zone in the amount of up to 2 moles per mole of RCN introduced into said reaction zone.

6. The reaction of claim 2 wherein water as a reaction promoter is introduced into the reaction zone in the amount of up to 10 moles per mole of RCN introduced into said reaction zone.

7. The reaction of claim 2 wherein water as a reaction promoter is introduced into the reaction zone in the amount of up to 2 moles per mole of RCN introduced into said reaction zone.

* * * * *